(12) United States Patent
Bege et al.

(10) Patent No.: US 12,721,538 B2
(45) Date of Patent: Sep. 1, 2026

(54) DEVICE FOR DETERMINING THE ABDOMINAL WALL DYNAMIC BIOMECHANICAL BEHAVIOR, AND A METHOD MAKING USE OF SUCH A DEVICE

(71) Applicants: UNIVERSITE D'AIX-MARSEILLE, Marseilles Cedex (FR); CENTRE NATIONAL DE LA RECHERCHE SCIENTIFIQUE, Paris (FR); ASSISTANCE PUBLIQUE—HOPITAUX DE MARSEILLE (AP-HM), Marseilles Cedex (FR); UNIVERSITE GUSTAVE EIFFEL, Marne-la-Vallee Cedex (FR)

(72) Inventors: Thierry Bege, Marseilles (FR); Julien Pagazani, Noisy le Grand (FR); Gaelle Lissorgues, Le Perreux sur Marne (FR); Arthur Jourdan, Marseilles (FR); Catherine Masson, Marseilles (FR); David Bendahan, Marseilles (FR)

(73) Assignees: UNIVERSITE D'AIX-MARSEILLE, Marseilles (FR); CENTRE NATIONAL DE LA RECHERCHE SCIENTIFIQUE, Paris (FR); ASSISTANCE PUBLIQUE—HOPITAUX DE MARSEILLE, Marseilles (FR); UNIVERSITE GUSTAVE EIFFEL, Marne-la-Vallee (FR)

( * ) Notice: Subject to any disclaimer, the term of this patent is extended or adjusted under 35 U.S.C. 154(b) by 429 days.

(21) Appl. No.: 18/029,627

(22) PCT Filed: Nov. 19, 2021

(86) PCT No.: PCT/EP2021/082378
§ 371 (c)(1),
(2) Date: Mar. 30, 2023

(87) PCT Pub. No.: WO2022/106661
PCT Pub. Date: May 27, 2022

(65) Prior Publication Data

US 2024/0049973 A1 Feb. 15, 2024

(30) Foreign Application Priority Data

Nov. 20, 2020 (EP) .................................... 20306418

(51) Int. Cl.
*A61B 5/03* (2006.01)
*A61B 5/00* (2006.01)

(52) U.S. Cl.
CPC .............. *A61B 5/03* (2013.01); *A61B 5/6831* (2013.01); *A61B 5/7275* (2013.01); *A61B 2562/0247* (2013.01)

(58) Field of Classification Search
CPC ....... A61B 5/03; A61B 5/6831; A61B 5/7275; A61B 2562/0247; A61B 5/4519; A61B 5/6823; A61B 5/6804; A61B 5/6805
See application file for complete search history.

(56) References Cited

U.S. PATENT DOCUMENTS 10,405,797 B1 9/2019 Uehara
10,814,166 B1 10/2020 Uehara
(Continued)

OTHER PUBLICATIONS

Stuart McGill, Daniel Juker, Peter Kropf, Appropriately placed surface EMG electrodes reflect deep muscle activity (psoas, quadratus lumborum, abdominal wall) in the lumbar spine, Journal of Biomechanics, vol. 29, Issue 11,1996, pp. 1503-1507, ISSN 0021-9290 (Year: 1996).*

*Primary Examiner* — Adam J Eiseman
*Assistant Examiner* — Lucy Eppert
(74) *Attorney, Agent, or Firm* — BakerHostetler

(57) ABSTRACT

A device for non-invasively evaluating or monitoring an intra-abdominal pressure and/or abdominal wall deformations and/or a risk of incisional hernia of a subject at a preventive stage and/or a pre-operative stage and/or a post-operative stage, the device includes an adjustable and flexible frame, the frame comprising a central area, a left lateral
(Continued)

area and a right lateral area; a network of main sensors suitable for measuring local deformations and/or local forces on the surface of the abdomen of the subject, the network of main sensors being assembled to the frame, wherein at least one main sensor is located in each area of the frame; connecting means adapted for connecting the network of main sensors to a treatment unit; and possibly positioning means adapted for positioning the device on the abdomen and/or adjustment means adapted for adjusting the device on the abdomen. The invention also relates to a system comprising a device and a treatment unit, and to a method for determining the abdominal wall dynamic biomechanical behavior of a subject, using a device or a system.

14 Claims, 7 Drawing Sheets

(56) References Cited

U.S. PATENT DOCUMENTS

| | | | | |
|---|---|---|---|---|
| 2005/0177059 | A1* | 8/2005 | Koivumaa | A61B 5/1038<br>600/546 |
| 2012/0035508 | A1* | 2/2012 | Van Leer | A61B 5/4356<br>600/588 |
| 2014/0174174 | A1 | 6/2014 | Uehara et al. | |
| 2015/0374280 | A1 | 12/2015 | Tomasi et al. | |
| 2016/0140866 | A1 | 5/2016 | Mcguire | |
| 2018/0192951 | A1* | 7/2018 | Amir | A61B 5/6805 |

* cited by examiner

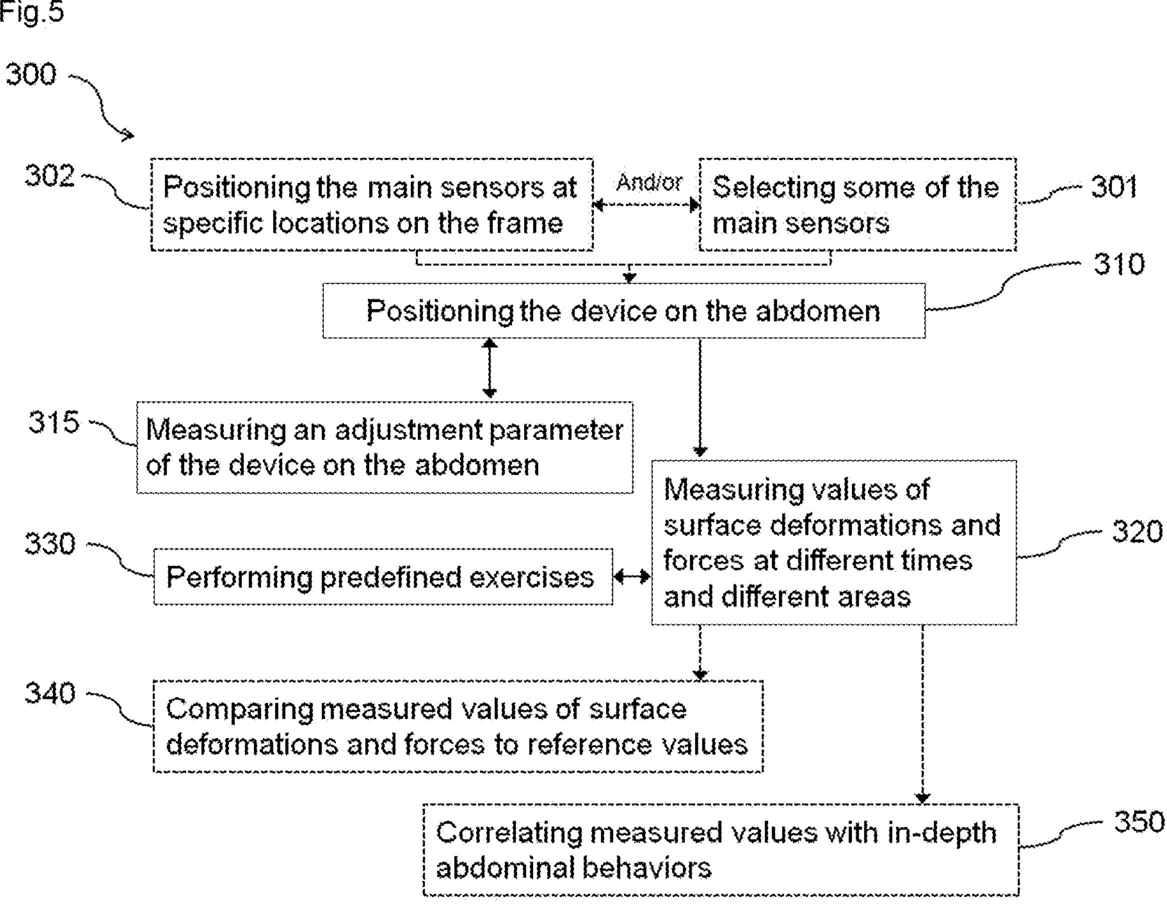
Fig.5
300
302
Positioning the main sensors at specific locations on the frame
And/or
Selecting some of the main sensors
301
Positioning the device on the abdomen
310
315
Measuring an adjustment parameter of the device on the abdomen
Measuring values of surface deformations and forces at different times and different areas
320
330
Performing predefined exercises
340
Comparing measured values of surface deformations and forces to reference values
Correlating measured values with in-depth abdominal behaviors
350

DEVICE FOR DETERMINING THE ABDOMINAL WALL DYNAMIC BIOMECHANICAL BEHAVIOR, AND A METHOD MAKING USE OF SUCH A DEVICE

CROSS-REFERENCE TO RELATED APPLICATIONS

This application is a National Stage of International patent application PCT/EP2021/082378, filed on Nov. 19, 2021, which claims priority to foreign European patent application No. EP 20306418.3, filed on Nov. 20, 2020, the disclosures of which are incorporated by reference in their entirety.

FIELD OF THE INVENTION

The invention relates to the abdominal wall of a person and to a device and a system for determining the abdominal wall dynamic biomechanical behavior, and a method making use of such a device or system. More particularly, the present invention relates to a device for non-invasively evaluating or monitoring an intra-abdominal pressure and/or a risk of incisional hernia of a subject at a preventive stage and/or a pre-operative stage and/or a post-operative stage

BACKGROUND

The abdominal wall most commonly refers to the anterolateral boundaries of the abdominal cavity. The abdominal wall is a complex, multi-layered structure. It is made up of the skin, subcutaneous fat layer as well as muscle layers surrounded by a sheet of connective tissue (fascia).

Depending on the level of the muscle activity, the roles of the abdominal wall are to maintain the viscera into the abdominal cavity, to contribute to breathing. The abdominal muscles also contribute to movements of the trunk, including flexion, extension, lateral flexion, and rotation. Simultaneous contraction of abdominal muscles can facilitate the generation of intra-abdominal and intrathoracic pressure critical in sneezing, coughing, vomiting, and defecating. This action may also help stabilize the trunk when lifting heavy loads. In times of increased physiological or pathological demand for airway ventilation, the anterolateral muscles (except transversus abdominis) act as accessory muscles of respiration by depressing the ribs to cause active expiration.

As illustrated in FIG. 1, the abdominal wall 100 is made up of four paired muscles, which are in the center the rectus abdominal muscle 101 and in the sides the external oblique, internal oblique and transverse muscles 102, 103. The linea alba corresponds to the fusion of the aponeurosis on the middle of the anterior wall and unites the rectus sheaths in the center of the abdomen 200.

Pathologies of the abdominal wall concern the damage to the muscles and fascia.

Ventral hernia, the most frequent abdominal wall pathology, corresponds to the protrusion of intra-abdominal contents through a muscular and fascia defect. These defects occur in case of the musculo-aponeurotic wall weakness and/or increased intra-abdominal pressure. The mechanism involved in the disruption of the abdominal wall is the application of a large tearing force on a small area of the abdomen. The musculo-aponeurotic weakness defects may be constitutional (natural orifice in umbilicus, epigastric . . . ) or are secondary to an abdominal surgery resulting in an incisional hernia at the site of the scar. The incidence of incisional hernias varies from 10% to 23% after a laparotomy or a laparoscopy, and can reach 38% in high-risk groups (smoking, obesity, etc.). Most of the incisional hernias occur in the linea alba.

Usually hernias cause discomfort and limit patients in their work or personal life. The serious complication of hernias is strangulation, which can be life-threatening, due to the obstruction and digestive necrosis it causes.

The treatment of symptomatic hernias requires operation, with closure of the defect and placement of a prosthetic implant. The results of this surgery remain largely perfectible, taking into account the high rate of recurrence (up to 28% at two years).

During clinical examinations, there are means for diagnosing ventral hernias. Some of the means consist in series of questions asked by the surgeon to the patient during the clinical examination. These are questions about the patient's lifestyle, such as smoking, activities, transit, occupation, etc. These questions are added to other elements regarding the patient's personal data and medical history such as obesity, pathologies with risk of infection, poor healing, etc.

The surgeon generally examines the patient to detect a presence of a ventral hernia, if so, measures the size of the collar and the volume of the hernia sac, allowing classifying the hernia according to the recommendations of the world hernia society. Additional preoperative paraclinical examinations (ultrasound or CT imaging of the abdominal wall) are reserved for complex situations or diagnostic doubts.

However, there is no preoperative means for evaluating the mechanical forces exerted on the abdominal wall or its compliance. These mechanical forces are however probably directly related to the evolutionary risk of a hernia (appearance of symptoms, increase in the size of the hernia), to the post-operative recovery (pain, speed of convalescence) and to the risk of recurrence at a distance from a repair.

The risk of formation of an incisional hernia after a surgical intervention on the abdomen cannot be easily predicted individually. There are also no objective means for post-operative follow-up or to guide the patient in post-operative recovery. Further to the absence of such means, there is no means adapted for providing information regarding the intra-abdominal pressure and abdominal wall mechanical behavior at a preventive stage, either for a single assessment or monitoring over time. Such information may help determining if a clinical or surgical intervention is required or not. Therefore, there is a need for easy-to-use and non-invasive means to evaluate or monitor intra-abdominal pressure and predict the risk of incisional hernia without the need for heavy means such as invasive catheter or radiating imaging examination. In some prior art methods, the intra-abdominal pressure is indirectly measured by measuring the intra-vesical pressure with a vesical probe connected to a pressure sensor. However such vesical probe is a source of infectious risks and is uncomfortable for the patient. Furthermore, such measurement method results in a discontinuous pressure measurement which is not suitable for the monitoring of intra-abdominal pressure.

US application 2015/0374280 A1 discloses a system for guiding a person in correct activation of his core muscles for a sport or other exercise session, comprising an at least partially elastic belt, sensor means comprising a 3D accelerometer sensor, a 3D gyroscope sensor and a 3D magnetometer sensor, means for evaluating the extensions and contractions of the belt and means for comparing the evaluation data and feedback means.

US application 2014/0174174 A1 discloses a system for development of core muscles' support comprising a means for identifying a user qualifying movement; a means for detecting a core muscle contraction; a means for discriminating between a core muscle contraction and no core muscle contraction, and a means to provide feedback to the user.

U.S. patent Ser. No. 10/814,166 B1 discloses a method for development of a core muscle, comprising providing a contraction sensor in a wearable device, adjusting the tension on the belt, detecting ambient musical notes, detecting core contractions of the user, transmitting core contraction signals, detecting a timing relationship between the core contractions and the ambient musical tones, analyzing the timing relationship and outputting correct and error signals.

U.S. patent Ser. No. 10/405,797 B1 discloses a method for detecting core muscle usage, comprising providing a contraction sensor, detecting a parameter related to a contraction status of the core muscles, converting the electrical signal into a digital value and determining the contraction status of the core muscle.

The invention seeks to overcome the aforementioned drawbacks of the prior art, and aims at providing a device for non-invasively evaluating or monitoring an intra-abdominal pressure and/or abdominal wall deformations and/or a risk of incisional hernia of a subject at a preventive stage and/or a pre-operative stage and/or a post-operative stage. For instance, the invention aims at providing a device for evaluating the risk of an incisional hernia formation after a surgical intervention on the abdomen. In other words, the invention aims at predicting the risk of rupture of a surgical repair of the abdominal musculo-aponeurotic wall (after laparotomy, laparoscopy or ventral hernia surgery).

Even further, the invention aims at providing a device for determining the abdominal wall dynamic biomechanical behavior, and a method making use of such device not only to evaluate the risk of an incisional hernia formation after a surgical intervention on the abdomen but also to evaluate the risk of post-operative effects like poor healing or weak muscle recovery, and to predict the evolutionary risk (appearance of symptoms or increase in size) in case of conservative treatment of a ventral hernia.

SUMMARY OF THE INVENTION

The inventors were able to demonstrate a correlation between the intra-abdominal pressure measured from within the abdomen and/or the musculo aponeurotic displacements of the abdominal wall on the one hand and the abdominal wall surface response measured by non-invasive sensors placed on the abdomen on the other. This work renders possible the use of a device comprising sensors, such as Force Sensitive Resistor (FSR) sensors, to be placed on the abdomen for recoding/measuring the abdominal wall surface behavior of a patient in order to evaluate/monitor the intra-abdominal pressure and abdominal deformations within the patient's abdomen and/or in order to evaluate the risk of incisional hernia. Advantageously, such device is not invasive and therefore heavy means such as invasive catheter or radiating imaging examination are no longer required for such evaluation/monitoring. Also, the device can be used simultaneously as a contention belt which allows preventing or decreasing the risk of incisional hernia while evaluating/monitoring said risk at the same time.

To this effect, the invention discloses a device for non-invasively evaluating or monitoring an intra-abdominal pressure and/or abdominal wall deformations and/or a risk of incisional hernia of a subject at a preventive stage and/or a pre-operative stage and/or a post-operative stage, said device comprising:

- an adjustable and flexible frame;
- a network of main sensors suitable for measuring local deformations and/or local forces on the surface of the abdomen of the subject, said at least one main sensors being assembled to the frame;
- connecting means for connecting said at least one main sensor to a treatment unit), and possibly:
- positioning means adapted for positioning the device on the abdomen and/or
- adjustment means adapted for adjusting the device on the abdomen.

Preferably, the frame comprises a central area, a left lateral area and a right lateral area, each area having a contact face adapted to face the skin of a subject and an opposed external face, the contact face of each area having an upper part adapted to face an hypochondrium or an epigastric part of the abdomen of a subject, a lower part adapted to face the hypogastrium region or an iliac part of the abdomen of a subject, and a middle part adapted to face the umbilic region or a flank part of the abdomen of a subject. Preferably, the contact face of each area is adapted to face the entire height of the abdomen, i.e. the central area faces the abdomen with an upper part of the central area facing the epigastric region, a middle part which faces the umbilic region and a lower part which faces the hypogastrium region, the left lateral area faces the abdomen with an upper part of the central area facing the left hypochondrium, a middle part facing the left flank and a lower part facing the left iliac region, the right lateral area faces the abdomen with an upper part of the central area facing the right hypochondrium, a middle part facing the right flank and a lower part facing the right iliac region.

By "non-invasively evaluating or monitoring an intra-abdominal pressure and/or abdominal wall deformations", it is meant that the device of the invention allows (i) evaluating an intra-abdominal pressure variation and/or abdominal wall deformations at a given time t and, for instance, provide the information to a practitioner or to a database or (ii) evaluating an intra-abdominal pressure variation and/or abdominal wall deformations at a first given time t, a second given time t+1 and optionally any further additional given time t+i, making it possible to assess the evolution of an intra-abdominal pressure variation. For instance, the device of the invention may be used to evaluate an intra-abdominal pressure variation and/or abdominal wall deformations at intervals of one day, one week or one month and this for one week, one month or several months. Such a monitoring allows identifying or not a predictive signal of an incisional hernia and determining if prophylactic actions should be carried out rather than curative actions.

By "an adjustable and flexible frame" it is meant a mean to which the network of main sensors may be assembled so that the network may be moved easily by manipulating such mean, the frame being wrapped around the patient's waist when used for evaluating an intra-abdominal pressure and/or abdominal wall deformations. By "adjustable", it is meant that the frame wrap a patient's waist and may be adjusted according to different tensions, which is taken into account for the evaluation of the intra-abdominal pressure variation and/or abdominal wall deformations.

Evaluating or monitoring an intra-abdominal pressure and abdominal wall deformations may be carried out using the device of the invention at a preventive stage, i.e. where no surgery or treatment has yet been performed or implemented or even scheduled. Evaluating and monitoring such intra-abdominal pressure and/or abdominal wall deformations at a preventive stage may help determine if a surgery should be performed or if a treatment should be implemented. Typically, the device of the invention can help determining whether a patient's incisional hernia needs to be operated or whether conservative treatment is sufficient as the device helps determine that there is a low risk of complications. The device may also be used at a post-operative stage as it may help determine if the surgery has been well performed and if there is a risk of recurrence. For instance, after a laparotomy the intra-abdominal pressure and/or the abdominal wall deformations may be monitored using the device of the invention in order to assess the risk of post-operative complication such as infection, by the early detection of an alteration in the physiological functioning of the wall in connection with a complication. The device may also be used as a tool to determine if an incisional hernia repair is strong enough to allow the patient to resume normal physical activity.

The device of the present invention allows the mapping of the properties of the abdominal wall, and particularly the deformations and/or passive elasticity of the abdominal wall, at a resting state and according to different movements of a subject, e.g. during breathing and/or during physiotherapy exercises.

Alternatively or additionally, the contact faces of the areas each have an upper part adapted to be adjusted on the costal margin of the abdomen of a subject, a lower part adapted to be adjusted to the iliac crests and/or the pubic symphysis and/or the inguinal region of the abdomen of a subject, and a middle part between the lower and the upper parts. By "being adjusted", it is meant that the part of the contact face of an area has a specific shape which comes into contact with the skin of the subject, directly or through a cloth which is thin enough not to affect a sensor measurement, at the closest to an anatomic part. For instance, by "adapted to be adjusted on the costal margin", it is meant that the part of the contact face of the area is in contact with the skin of the subject at the closest location to the costal margin. As a results, the frame comprising the central area, the left lateral area and the right lateral area, is adapted to fit to the anterolateral face of the abdomen.

According to these alternatives or to their combination, the length of the lower parts, the middle parts and the upper parts of each area along the vertical axis of a subject are preferably equal between each other, i.e. correspond to about a third of the length of the abdomen along its vertical axis. Consequently, as the device is positioned on the abdomen and preferably centered on the umbilic region, the central area may be substantially longer than the left or right areas due to the shape of an abdomen. Hence, the central area may have an upper part adapted to be adjusted to the costal margin, i.e. adjoining the xyphoid process for the central area, and a lower part adapted to be adjusted to the pubic symphysis. In some embodiments, the width of any of the area (central, left and right) corresponds to 20 to 50 percent of the total width of the anterolateral face of the abdomen, with a total of 100 percent. In some embodiments, the height of any of the area (central, left and right) corresponds to 20 to 50 percent of the total height of the anterolateral face of the abdomen, with a total of 100 percent. Also, in one particular embodiment, the widths and heights of the areas may be substantially equal between each other, i.e. correspond to about a third of the width or height of the abdomen. In any case, these proportions can be adapted to each patient's morphology.

Preferably, in a particular embodiment which may be combined to any other embodiment, the device does not comprise sensors which are located so as to face the posterior face of the abdomen. Notably, the device does not comprise sensors which are located so as to face the following muscles: the serratus posterior inferior muscle, the latissimus dorsi or the quadratus lumborum muscle.

Connecting means may be connectors and/or wireless means.

The device may also comprise positioning means for positioning the device on the abdomen and/or adjustment means for adjusting the device on the abdomen.

The subject designates a person. The main sensors are non-invasive sensors. A "non-invasive" sensor means that the sensor is placed on and outside the body of the subject, is painless and risk-free for the subject.

The frame is adjustable and flexible in order to allow positioning the frame, and thus the device, on the abdomen of the subject, whatever the morphometry or morphology of the abdomen of the subject.

Preferably, the flexible frame is suitable for restraining the abdomen. Particularly, the device of the invention may be used as a contention belt.

The frame may be made in an elastic material such as an elastic fabric.

The device is adapted to be positioned on the abdomen of the subject, directly on the skin or indirectly for instance through a thin fabric or a cloth.

Although this is well known by the skilled person of the art, it is recalled that biomechanics is the study of the mechanical aspects of biological systems such as humans systems in terms of structure, function and motion . . . . The dynamic biomechanical behavior of the abdominal wall means the spatio-temporal response of the abdominal wall. The device of the present invention allows evaluating or monitoring an intra-abdominal pressure and/or abdominal wall deformations and/or a risk of incisional hernia and not only the behavior of the muscles of the abdominal wall.

According to the invention, the abdominal wall dynamic biomechanical behavior is determined using the measurement of deformation and force (such as pressure) sustained by the abdominal wall, the measures being provided by at least the main sensors. The dynamic biomechanical behavior of the abdominal wall is mainly determined by the response of the antero-lateral muscles and the aponeurosis of the abdomen, but is not limited to the muscle activity only. The notion of dynamics also generally corresponds to the temporal evolution of the abdominal wall response during a movement and/or one of the predefined exercises.

"Predefined exercises" are exercises which must have an impact on the abdominal muscle work and that are defined in advance. The predefined exercises may include abdominal muscle contractions, pushing efforts, breathing exercises, cough, forced breathing, valsalva and weight lifting. The exercises are generally explained by the medical team and are performed by the subject.

Due to the physical nature of the hernia, it is said to be impulsive and expansive. In other words, hernia becomes more and more visible (therefore an increase in volume) during exercises having an impact on the abdominal muscles work. Thus, the exercises are done so that the hernia appears.

The measured values of deformations and/or forces may be displayed, for instance to the subject or to a practitioner. Thus the subject or the practitioner may see the measurements during or after the measurements when previously recorded.

The measured values of deformations and/or forces are recorded and/or analyzed. Both deformations and forces may be combined for the analysis.

The device according to the invention may also include one or more of the following characteristics taken in isolation or in any possible technical combination.

According to a preferred embodiment, the device comprises a network of main sensors positioned at different locations on the frame, notably at least one main sensor in each area. In a preferred embodiment, at least one main sensor is located in each part of each area of the frame, and possibly according to different orientations. When the device comprises at least one main sensor in each part of each area of the frame, it is possible to monitor the abdominal wall deformations of the entirety of a patient's abdomen as well as the intra-abdominal pressure, which allows obtaining more reliable information regarding the evolution of these deformations and of this pressure, as well as allowing the complete mapping of the abdomen. Such mapping also allows determining if an evolution of these deformations or of this pressure results from an overall evolution in every area or if data obtained from specific areas shows a different evolution from the other areas.

In one embodiment, the device comprises a network of 6, 7, 8, 9, 10, 11, 12, 13, 14, 15, 16, 17, 18 or more main sensors on the frame wherein at least one sensor is located in each part (upper, middle and lower part) of each area (left lateral, central and right lateral area) of the frame. Preferably the device comprises a network of at least 14, preferably 15 or even preferably 16 main sensors wherein at least one sensor is located in each part (upper, middle and lower part) of each area (left, central and right area) of the frame.

Having a network of sensors allows to measure surface deformations and forces at different areas of the abdominal wall. This enables creating a mapping of surface abdominal deformations and forces.

Preferably, the main sensors of the network are distributed in order to cover specific areas in the abdominal wall, preferably in the anterolateral abdominal wall.

The specific areas may be centered on the umbilicus.

The specific areas may comprise at least one location in at least one of the four quadrants and/or in at least one of the nine regions of the abdomen.

The specific areas may comprise at least one location in the four quadrants and/or in the nine regions of the abdomen.

Although this is well known by the skilled person of the art, it is recalled that the human abdomen is divided into four quadrants (left lower, left upper, right lower, right upper) and nine regions (epigastric, umbilical, hypogastric, left and right hypochondriac, left and right lumbar flank, left and right iliac or inguinal regions) for the purposes of study, diagnosis, and treatment.

The network of main sensors may comprise different types of sensors.

According to an advantageous embodiment, the main sensors are repositionable at different locations on the frame. For instance, the device comprises Velcro tapes both on said sensor and on the frame. Other means adapted for (re) positioning the main sensor(s) may be used, such as a push-button, a staple, an adhesive tape, adhesive paste . . . .

According to a particular embodiment, the number of main sensors of the device is adaptable.

The device may comprise at least one additional sensor also suitable for measuring local deformations and/or local forces on the surface of the abdomen of the subject, but being not assembled to the frame. The additional sensor is a non-invasive sensor. The device may also comprise means for connecting said at least one additional sensor to the treatment unit.

According to an embodiment, the device further comprises at least an adjustment sensor suitable for measuring an adjustment parameter of the device on the abdomen, and means for connecting said at least one adjustment sensor to the treatment unit. The adjustment sensor is a non-invasive sensor.

The adjustment parameter corresponds to the contact force or tension of the device on the abdomen. Indeed, the contact force or tension, measured by said adjustment sensor, must generally be adjusted in order to ensure the reliability and the reproducibility of the measures.

According to an embodiment, the device comprises control means for controlling that the adjustment parameter of the device on the abdomen is equal to a predefined value or comprised in a predefined range. It may be standardized ranges of the initial adjustment parameter of the device around the abdomen (such as a belt tension).

According to an embodiment, the device comprises adjustment means for adjusting the device on the abdomen of the subject depending on the subject morphology, in particular for modifying the adjustment parameter of the device on the abdomen. The adjustment means may be Velcro tapes on the frame. Other adjustment means may be used, such as push-buttons, straps . . . .

The device may have different sizes, depending on morphometry or morphology of the subject.

According to an embodiment, the device comprises positioning means for positioning the device on the abdomen. Positioning means may comprise a placement guide. A placement guide may be a visual marker such as a cross, a color . . . . The placement guide may be connected to the treatment unit.

The at least one main sensor and/or the at least one additional sensor and/or the at least one adjustment sensor may be: a resistive sensor, for instance a force sensing resistor (FSR) or another piezoresistive sensor, a piezoelectric sensor, a pneumatic sensor, an electromyography (EMG) sensor, a capacitive sensor or a combination of several of said sensors. In a preferred embodiment, the main sensors are FSR sensors, even preferably tongue-shaped FSR sensors. FSR sensors are advantageously used since this type of sensor is able to measure/monitor several types of mechanical stress. In the frame of the invention, FSR sensors car measure/monitor the variation of pressure directly applied on it but also its mechanical deformation for example by flexion. Therefore the FSR sensors are particularly adapted to the objective of the invention, in order to evaluate or monitor the intra-abdominal pressure and the abdominal wall deformations.

According to an advantageous embodiment, the at least one main sensor and/or the at least one adjustment sensor is flexible. It makes said sensors enabled to follow the shape of the abdomen when attached to the frame. Flexible sensors may be piezoresistive sensors, piezoelectric sensors . . . .

According to an embodiment, the device is a connected-device.

By "connected-device", it should be understood that the device is connected to the Web/Internet by a wired and/or wireless connection (Bluetooth, Wi-Fi, etc.).

The device may comprise a network communication interface. The network communication interface may be wired or wireless or both wired and wireless.

The device may comprise on-board electronics connected to the at least one main sensor (and/or the at least one adjustment sensor and/or the at least one additional sensor) using a wired connexion. The on-board electronics may also comprise a Bluetooth module in order to enable a Bluetooth pairing with the treatment unit, for instance with a desktop computer, a laptop, a tablet, a smartphone . . . .

The device may also comprise a battery that may be integrated in or with the on-board electronics.

According to an embodiment, the device is designed in order to cover the entire or almost the entire abdominal wall, preferably the anterolateral abdominal wall.

According to an embodiment, the adjustable and flexible frame is a belt, preferably an elastic belt. According to a particular embodiment, the adjustment parameter of the device corresponds to the belt tightening tension. The adjustment means may be Velcro tapes on the belt. Other adjustment means may be used, such as push-buttons, straps . . . .

A second object of the invention is a system for non-invasively evaluating or monitoring an intra-abdominal pressure and abdominal wall deformations and/or a risk of incisional hernia of a subject at a preventive stage and/or a pre-operative stage and/or a post-operative stage, the system comprising the device according to the first object of the invention and a treatment unit connected to said device and able to:

- display all or part of the measured values, and/or
- record all or part of the measured values, and/or
- treat or analyze all or part of the measured values, and/or
- select some of the main sensors, and/or
- control and/or adjust the adjustment parameter of the device on the abdominal wall.

According to an embodiment, the treatment unit comprises a desktop computer, a laptop computer, a tablet, a smartphone . . . .

A Web App or a mobile App may be implemented in the treatment unit, for instance in the desktop or laptop computer, the tablet or the smartphone. The App may be at least adapted to treat, to record and/or to display the measured data.

According to one embodiment, the device further comprises on-board electronics connected with a wired connexion to the main sensors (and/or the at least one adjustment sensor), said on-board electronics being wireless connected to the treatment unit.

A third object of the invention is the use of the device as previously described or of the system as previously described for non-invasively evaluating or monitoring an intra-abdominal pressure and/or abdominal wall deformations and/or a risk of incisional hernia of a subject at a preventive stage and/or a pre-operative stage and/or a post-operative stage.

In particular the third object of the invention is the use of a device for non-invasively evaluating or monitoring an intra-abdominal pressure and/or abdominal wall deformations and/or a risk of incisional hernia of a subject at a preventive stage and/or a pre-operative stage and/or a post-operative stage wherein said device comprises:

- an adjustable and flexible frame, the frame comprising a central area, a left lateral area and a right lateral area, each area having a contact face adapted to face the skin of a subject and an opposed external face, the contact face of each area having an upper part adapted to face an hypochondrium or an epigastric part of the abdomen of a subject, a lower part adapted to face the hypogastrium region or an iliac part of the abdomen of a subject, and a middle part adapted to face the umbilic region or a flank part of the abdomen of a subject;
- a network of main sensors suitable for measuring local deformations and/or local forces on the surface of the abdomen of the subject, said network of main sensors being assembled to the frame, wherein at least one main sensor is located in each area of the frame;
- connecting means adapted for connecting said network of main sensors to a treatment unit; and possibly:
- positioning means adapted for positioning the device on the abdomen and/or adjustment means adapted for adjusting the device on the abdomen In particular the third object of the invention is the use of a system for non-invasively evaluating or monitoring an intra-abdominal pressure and/or abdominal wall deformations and/or a risk of incisional hernia of a subject at a preventive stage and/or a pre-operative stage and/or a post-operative stage, said system comprising a device as previously described and a treatment unit connected to the device and able to:

- display all or part of the measured values, and/or
- record all or part of the measured values, and/or
- treat or analyze all or part of the measured values, and/or
- select some of the main sensors, and/or
- control and/or adjust the adjustment parameter of the device on the abdominal wall A fourth object of the invention is a method for non-invasively evaluating or monitoring an intra-abdominal pressure and/or abdominal wall deformations and/or a risk of incisional hernia of a subject at a preventive stage and/or a pre-operative stage and/or a post-operative stage, said method using a device according to the first object of the invention or a system according to the second object of the invention, and comprising:

- a positioning step adapted to position the device on the abdomen of the subject in such a way that the network of main sensors faces the abdominal wall, said main sensors being placed on the abdominal wall;
- a measuring step adapted to measure values of surface deformations and/or forces on the surface of the abdomen at different times, for at least a given period of time, in order to obtain a temporal evolution of the surface deformations and/or forces.

The device and/or the at least one main sensor may be positioned directly on the abdomen of the subject, or indirectly for instance through a fabric, a cloth . . . .

The method is able to determine the dynamic biomechanical behavior of the abdominal wall, using at least some of the measured values of surface deformations and/or forces. The method of the present invention therefore allows mapping the properties of the abdominal wall, and particularly the deformations and/or passive elasticity of the abdominal wall, at a resting state and according to different movements of a subject, e.g. during breathing and/or during physiotherapy exercises.

The method may comprise an additional positioning step adapted to position at least one additional sensor on the abdomen of the subject, and also an additional measuring step adapted to measure values of surface deformations and/or forces using said at least one additional sensor.

According to an embodiment, wherein the device comprises a network of main sensors, possibly different types of main sensors, positioned at different locations on the frame in order to face different areas of the abdominal wall, the measuring step comprises measuring surface deformations and forces at different areas of the abdominal wall. This enables creating a mapping of surface abdominal deformations and forces.

The method may comprise a step of positioning the main sensors at specific locations on the frame, in order to measure values of surface deformations and forces at defined and specific areas. The main sensors may be repositionable.

In one particular embodiment, the method comprises a selecting step adapted to select some of the network of the main sensors, possibly different types of main sensors, in order to measure values of surface deformations and forces at specific areas. This covers the case where the main sensors are already attached on the frame at different positions, but where only some of said sensors are used.

According to one embodiment, the method comprises a step of performing exercises, in which the subject performs different predefined exercises during all or part of the measuring step. The predefined exercises were previously defined.

The method may comprise at least one of the following steps:

- a recording step for recording all or part of the measured values of surface deformations and/or forces;
- a displaying step for displaying all or part of the measured values,
- an analyzing step for analyzing all or part of the measured values.

The analysis of the measured values may serve to classify the subject in comparison with the values of other subjects, or to make other comparisons.

According to one embodiment, the method comprises a comparing step, adapted to compare all of part of the measured values of surface deformations and forces to reference values.

According to one particular embodiment, the reference values are based on values of surface deformations and/or forces available for at least another subject or panel of subjects, being reference subject(s).

Alternately, the reference values may be obtained by numerical simulations.

According to one embodiment, the method comprises a correlation step, adapted to correlate the measured values with in-depth abdominal behaviors.

In one embodiment, the correlation step is suitable for correlating the measured values of surface deformations and/or forces with criteria defining a level of risk of rupture in the abdominal wall, for instance a level of risk of ventral hernia or incisional hernia in the abdominal wall.

In one embodiment, the correlation step comprises correlations developed between surface deformations and/or forces values measured for at least a subject performing at least a predefined exercise and medical imaging, for instance using MRI and/or ingested pressure sensor, carried out for the at least one subject performing the at least one predefined exercise.

In one particular embodiment, the correlation step comprises a technique of statistical correlation or machine learning (supervised, unsupervised or deep on the collected data).

According to one embodiment, the method comprises a step of determining a level of risk of rupture in the abdominal wall, for instance level of risk of ventral incisional hernia, using the measured values.

In one particular embodiment, the method comprises a step of activating an alert if the level of risk excesses a predefined threshold.

According to one embodiment, the positioning step comprises using at least a placement guide, for instance a visual marker as a cross, a color . . . . For instance, a cross or a color may be used to center the device on the umbilicus. The placement guide may be connected to the treatment unit.

According to one embodiment, where the device comprises at least an adjustment sensor, the method comprises a step of measuring an adjustment parameter of the device on the abdominal wall.

The method may comprise a controlling step for controlling if the adjustment parameter of the device on the abdominal wall is equal to a predefined value or is comprised in a predefined range.

The method may comprise an adjustment step for adjusting the device on the abdomen of a subject depending on the subject morphology, in particular for modifying the adjustment parameter of the device on the abdominal wall.

The adjustment step may consist in tightening or loosening the frame around the abdomen of the subject, for instance if the frame is a belt. This may be done using Velcro tapes on the frame, in order to adjust the adjustment parameter to the predefined value or the predefined range. Said predefined value or predefined range may serve as a reference for the examination of different subjects.

The device, the system and the method according to the invention can include any of the previously stated characteristics, taken in isolation or in any technically possible combination with other characteristics.

BRIEF DESCRIPTION OF THE DRAWINGS

The invention will be better understood and its various characteristics and advantages will emerge from the following description of a number of exemplary embodiments and its appended figures in which:

FIG. 5 represents an exemplary method of the invention;

DETAILED DESCRIPTION

In this specification, the invention will be described by way of examples. However, the invention is not restricted to these examples.

Figure 1:
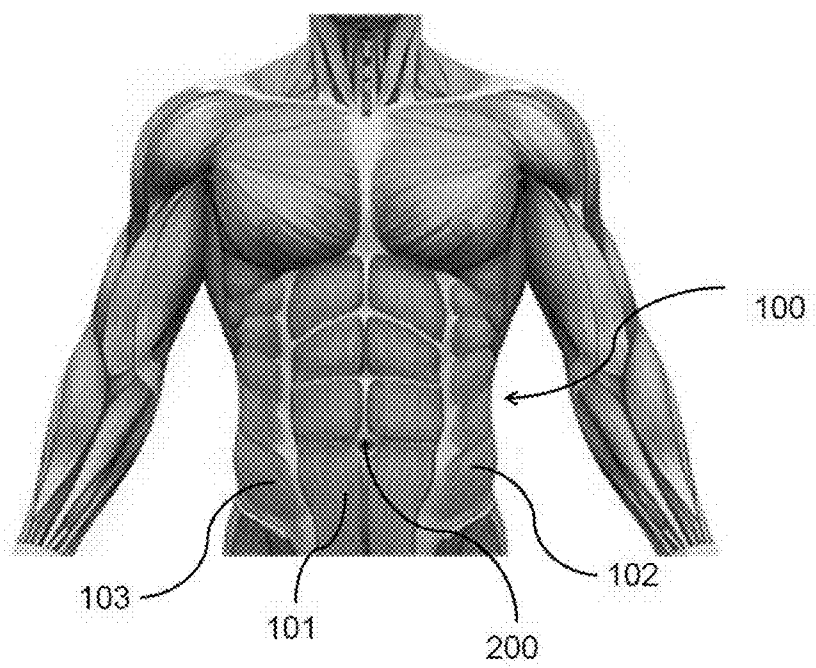
FIG. 1 illustrates an abdominal wall.

FIG. 1 has already been described and will not be repeated here.

Figure 2:
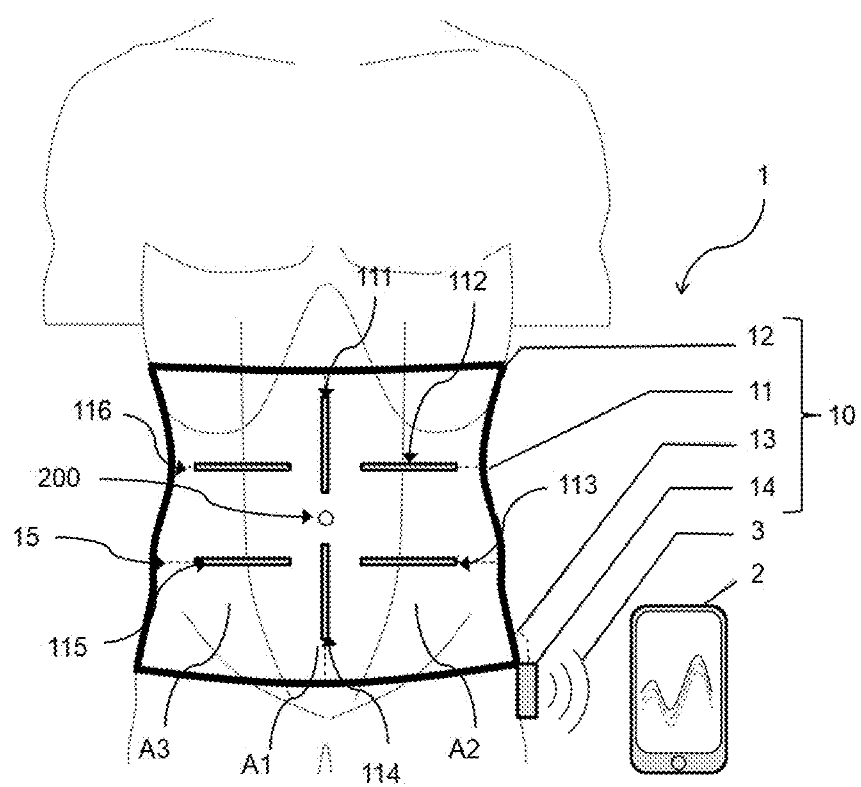
FIG. 2 represents an exemplary device and system of the invention.

FIG. 2 represents an exemplary device 10 and an exemplary system 1 of the invention.

The illustrated device 10 comprises a frame 12 which is a belt made of an elastic fabric suitable for restraining the abdomen. Thus, the belt forming the frame is flexible. In addition, the belt is adjustable to the abdomen of the subject using Velcro tapes (not shown) which are in the back of the subject. Thanks to the Velcro tapes, the belt may be adaptable to almost any body type.

The belt may be a thoracic-abdominal support belt. A thoracic-abdominal support belt is suitable for the invention because it is elastic, it correctly supports the back and the abdomen, and allows the sensors to be close to the body, and especially to the abdominal wall.

The belt may have a height adapted to cover the entire abdominal wall, for instance comprised between 20 and 30 centimeters.

The belt may also exist in several different sizes in order to cover all body types (morphology, etc. . . . ).

The illustrated device comprises a plurality (a network 11) of main sensors placed on the belt (on the side of the belt that is meant to face the abdomen). The main sensors are suitable for measuring local deformations and/or local forces on the surface of the abdomen. A network 11 of six main sensors 111-116 is represented, which are elongated sensors.

Figure 3:
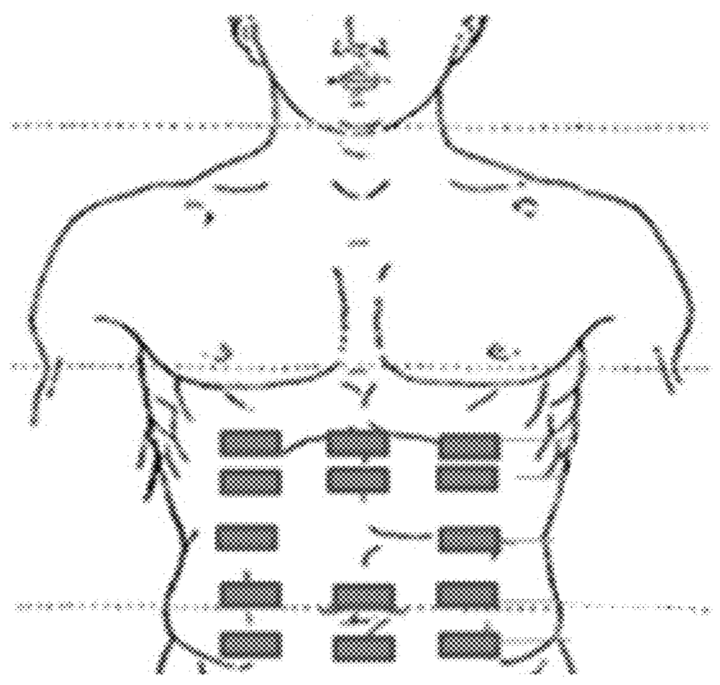
FIG. 3 represents a variation of the device and system of FIG. 2 comprising more main sensors.

The number of six main sensors is not limitative and more (or less) main sensors may be included in the network, for instance fourteen main sensors as illustrated in FIG. 3 representing a variation of the device and system of FIG. 2 comprising more main sensors. Also the dimensions of the main sensors may be different.

For example, the length of a sensor may be around five centimeters and the width around five millimeters, and the thickness may be about one millimeter or below one millimeter.

The six main sensors are positioned in three main areas with two sensors by area. Referring also to FIG. 1 and observing the subject to the front: the first area A1 corresponds to the rectus abdominal muscle 101 (in the center), the second area A2 corresponds to the right broad abdominal muscles 102 and the third area A3 corresponds to the left broad abdominal muscles 103.

In the first area A1, two sensors 111, 114 are positioned and orientated in the vertical direction. More precisely, the two sensors 111, 114 are positioned in the line that goes through the middle of the rectus muscles and passing through the umbilicus 200, this line being particularly subject to a risk of formation of hernias. Sensor 111 is located in the upper part and sensor 114 located in the lower part.

In the second area A2, two sensors 112, 113 are positioned and orientated in the horizontal direction. Sensor 112 is located in the upper part and sensor 113 is located in the lower part.

In the third area A3, two sensors 115, 116 are positioned and orientated in the horizontal direction. Sensor 116 is located in the upper part and sensor 115 located in the lower part.

The main sensors chosen in the exemplary device 10 are Force Sensing Resistor (FSR) sensors. FSR sensor is a resistive force sensor in which a resistance is modified depending on the pressure applied to it and or on its deformation (such as its flexion). The FSR are interesting sensors for the invention since this type of sensor is able to measure/monitor several types of mechanical stress (pressure variation and mechanical deformation). It is particularly adapted in the context of the invention wherein the abdominal wall can be exposed to pressure (from within the abdomen) but also to tissue expansion (as a result of a growing intrabdominal pressure). FSR sensors exist in different sizes, shapes and dimensions for a very varied use. The FSR sensors chosen in the exemplary device 10 have the shape of flexible bands.

Alternately, the main sensors may be another piezoresistive sensor, a piezoelectric sensor, a pneumatic sensor, an electromyography (EMG) sensor, a capacitive sensor or a combination of several of said sensors.

For instance a piezoelectric sensor provides dynamic (high frequency) deformation and force values of transient variations unlike FSR sensor which gives low frequency deformation and force values and static state. Thus, using at least one of each sensor may be useful to have two different types of values.

An EMG sensor allows detecting muscle activity using electrodes and recording electrical signal which are corresponding to contraction-dependent voltages.

At least some of the main sensors are repositionable. For instance, some sensors may comprise a Velcro tape able to cooperate with another Velcro tape located on the belt. Other means adapted for (re)positioning the main sensor(s) may be used, such as a push-button, a staple, an adhesive tape, adhesive paste . . . .

It is to be noted that the device may comprise additional sensors also suitable for measuring local deformations and/or local forces on the surface of the abdomen of the subject, but being not assembled to the frame. For instance, electromyography sensors (EMG) may be placed directly on the skin between the device and the skin. EMG sensors have at least two electrodes placed directly on the skin.

The device comprises on-board electronics in a housing 14, which may also integrate a battery (not shown). The housing may be assembled to the device in a front side of the belt. The housing may be assembled to the device using Velcro tapes or other adapted assembling means. The housing may form a small pocket.

Each sensor is connected to the electronics in the housing 14 using wired connexions (dotted lines 15). All the wired connexions are not shown.

The on-board electronics comprises a Bluetooth module in order to enable a Bluetooth pairing 3 with a treatment unit. The represented treatment unit 2 is a smartphone.

A Web App or a mobile App may be implemented in the smartphone, the App being at least adapted to display and/or treat the measured data.

Figure 4:
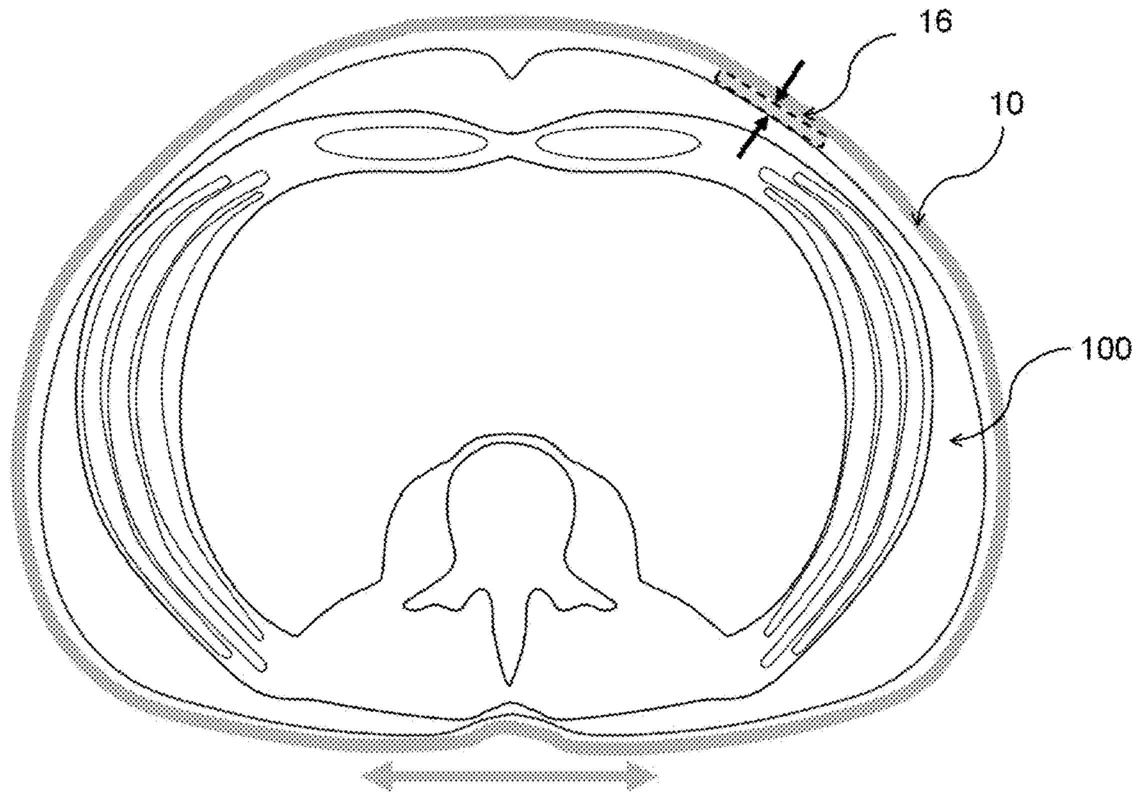
FIG. 4 represents a sectional view of a device according to the invention placed on the surface of the abdomen, the device comprising an adjustment sensor placed between the device and the abdomen.

FIG. 4 represents a sectional view of a device 10 according to the invention placed on the surface of the abdomen 100, the device comprising an adjustment sensor 16 placed between the device and the abdomen. It also represents the adjustment of the frame (belt) around the abdomen. It shows how the frame is correctly stuck against the abdomen.

FIG. 5 represents an exemplary method of the invention using a device comprising a network of sensors, such as the device of FIG. 2.

First, the illustrated method 300 may comprise one or two of the following preliminary steps:

- a step 301 for positioning the main sensors at specific locations of the device; and/or
- a selecting step 302 for selecting some of the main sensors which are already attached to the device.

Then the method comprises the following steps:

- a positioning step 310 adapted to position the device on the abdomen of a subject in such a way that the main sensors face the abdominal wall, said main sensors being placed on the abdominal wall;

a measuring step 320 adapted to measure values of surface deformations and/or forces on the surface of the abdomen at different times, for at least a given period of time, in order to obtain a temporal evolution of the surface deformations and/or forces;

a step 330 of performing different predefined exercises, in which the subject performs different predefined exercises during all or part of the step of measuring exercises.

The device may be worn by a subject for a given time or at several different times (time during which different exercises are made by the subject for example) or may be worn by the subject during a continuous period of time. For instance, the subject with the device may be monitored over a long time of the signal. A long time may correspond to a few hours to one day, or more. The device may be worn for monitoring at home, in a medical center or hospital.

The predefined exercises may include abdominal muscle contractions, pushing efforts, breathing exercises, cough, forced breathing, valsalva and weight lifting. The exercises are explained by the medical team.

After having collected the measured values of surface deformations and/or forces, the method may comprise one of two of the following steps:

a comparing step 340 adapted to compare measured values of surface deformations and forces to reference values; and/or a correlation step 350 adapted to correlate the measured values with in-depth abdominal behaviors.

The method may also comprise at least one of the following steps (not shown):

a recording step for recording all or part of the measured values of surface deformations and/or forces;

a displaying step for displaying all or part of the measured values, an analyzing step for analyzing all or part of the measured values.

The measured values delivered by the sensors may be transmitted as signals to acquisition means located on or attached to the frame, for instance to the on-board electronics connected to each sensor. The signals may be transmitted from the acquisition unit by a wireless connection (Bluetooth, Wi-Fi, etc.) in order to be controlled on a screen (desktop computer, laptop computer, tablet, smartphone . . . ).

The measured values may be analyzed in order to determine a response profile, taking into account the amplitude of the values and/or their evolution over time according to its location on the abdomen. The method may use machine learning to define the response profile of a subject.

The response profile of a subject may be compared to the response profile of other subjects with or without abdominal wall abnormalities and/or to a referenced profile.

The measured values may be correlated with in-depth abdominal behaviors. Thus, the response profile of the abdominal wall surface may reflect the mechanical behavior of the deep muscular wall. The link between the surface signal and deep muscle behavior may be previously validated by a correlation analysis between surface signals and deep muscle deformities (obtained by dynamic MRI) and intra-abdominal pressures (by ingested pressure sensors).

The response profile may allow predicting the aftermath of a surgical operation on the abdomen (laparotomy, laparoscopy, hernia or incisional hernia n treatment) such as: postoperative pain, speed of recovery, time of solidity of convalescence, risk of recurrence.

Depending on the level of a determined level of risk of hernia or incisional hernia, modifications to the post-operation of the abdomen may be proposed (use of prosthesis, etc.).

The response profile makes it possible to determine a maximum level of activity for a subject postoperatively after an intervention on the abdomen.

The evolution of the response profile of a subject makes it possible to follow the evolution of intra-abdominal pressures and/or abdominal wall deformations, in particular in the context of abdominal compartment syndrome for subjects in intensive care.

The device and the method may be used to monitor deformations and force of the abdominal wall during daily life.

The device may be used in post-operation for a given period (for instance a month) to relieve pain and tension on scar tissue. The device may also be useful during this period to detect "risky" or "unfavorable" situations for good healing.

Figure 6:
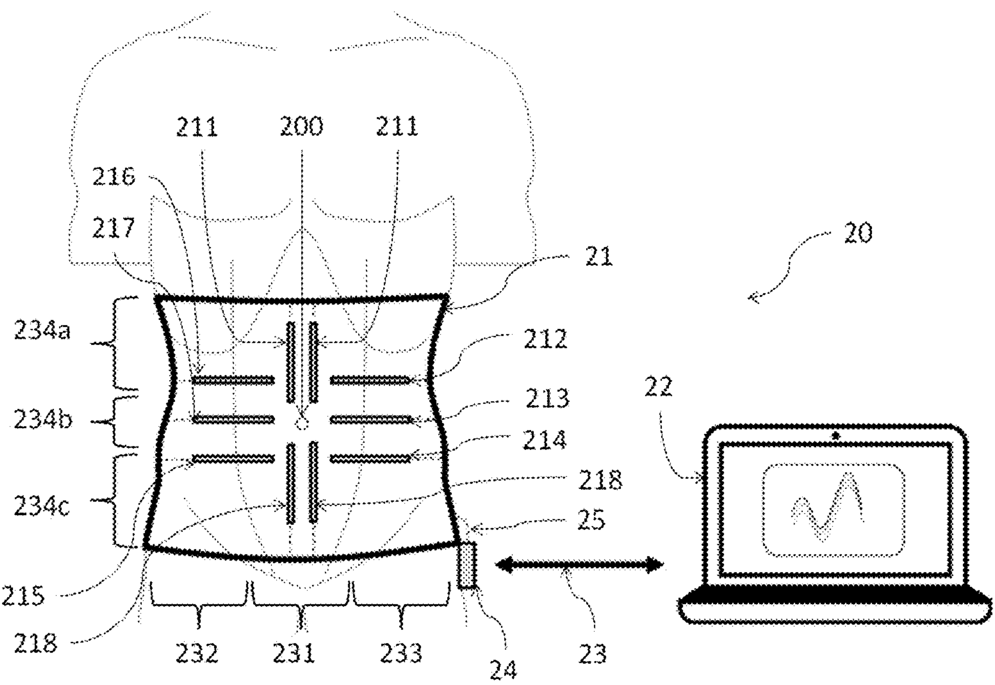
FIG. 6 represents an exemplary device and system of the invention.

FIG. 6 illustrates a device 20 comprising a frame 21 which corresponds to a belt which may be made of an elastic fabric suitable for restraining the abdomen. Thus, the belt forming the frame is flexible. In addition, the belt is adjustable to the abdomen of the subject using Velcro tapes (not shown) which are in the back of the subject and may be used as a contention belt if necessary. Thanks to the Velcro tapes, the belt may be adaptable to almost any body type. Other adjustable means than Velcro tapes may be used such as straps or elastic fabric with fasteners.

The belt may have a height adapted to cover the entire abdominal wall, for instance comprised between 20 and 30 centimeters although other sizes may be used to adapt to subject having larger bodies.

The illustrated device comprises a network of main sensors 211-218 placed on the belt (on the face of the belt that is meant to face the abdomen). The main sensors are suitable for measuring local deformations and/or local forces on the surface of the abdomen. A network 21 of ten main sensors 211-218 is represented, which are elongated FSR sensors.

The number of ten main sensors is not limitative and more (or less) main sensors may be included in the network. Also the dimensions of the main sensors may be different. For example, the length of a sensor may be around five centimeters and the width around five millimeters, and the thickness may be about one millimeter or below one millimeter.

The frame 21 comprises three areas which are the central area 231, the right lateral area 232 and the left lateral area 232. These areas may be further divided in parts according to the height of the abdomen, i.e. according to the upper height 234*a*, the central height 234*b* and the lower height 234*c*. These areas, heights and parts as represented in FIG. 6 do not limit the invention to the device in FIG. 6 as the sizes of the areas, of the heights, and therefore the sizes of the parts, may differ.

The ten main sensors as in FIG. 6 are positioned in the three areas 231, 232, 233 with one or multiple sensors by area. The sensors 211 and 218 are substantially parallel to the longitudinal axis (craniocaudal axis) and are positioned in the central area 231 of the belt. Therefore sensors 211 and 218 are positioned in the line that goes through the middle of the rectus muscles and passing through the umbilicus 200. Sensors 211 are located from the upper part to the umbilicus 200 while sensors 218 are located from the umbilicus to the lower part. The sensors 212-217 are substantially perpendicular to the longitudinal axis and substantially parallel to the horizontal axis (frontal axis), the sensors 212, 213 and 214 being in the left lateral area 233 of the belt, and the sensors 215, 216 and 217 being in a the right lateral area 232 of the belt. Regarding the longitudinal axis, sensors 212 and 216 are located in the upper part, i.e. at the upper height 234*a* of the abdomen, sensors 213 and 217 in the middle part, i.e. at the central height 234*b*, and sensors 214 and 215 in the lower part, i.e. at the lower height 234*c*. Each main sensor may be located in a unique area or may be located in multiple areas according to its length. In FIG. 6, main sensors 212, 213 and 214, though mainly located in the left lateral area 233, are also partially located in the central area 231. Similarly, main sensors 215, 216 and 217 are mainly located in the right lateral area 232 but are also partially located in the central area 231.

The device comprises on-board electronics in a housing 24, which may also integrate a battery (not shown). The housing may be assembled to the device in a front side of the belt. The housing may be assembled to the device using Velcro tapes or other adapted assembling means. The housing may form a small pocket.

Each sensor of the network is connected to the electronics in the housing 14 using wired connexions (dotted lines 25). All the wired connexions are not shown.

The on-board electronics comprises a Bluetooth module in order to enable a Bluetooth pairing 23 with a treatment unit 22. The represented treatment unit 22 is a computer although it may be a smartphone or other device able to receive and display the data obtained from the sensors.

Figure 7:
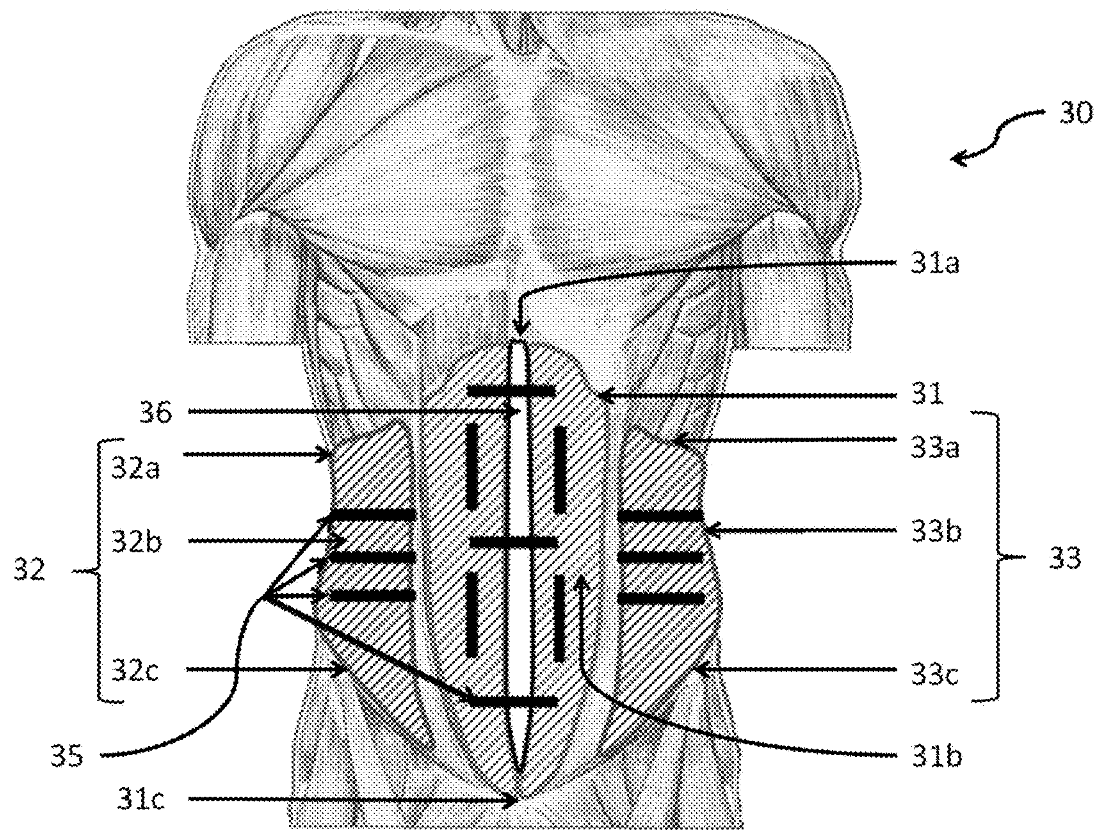
FIG. 7 represents a preferred embodiment of the device and system of the invention.

FIG. 7 illustrates a preferred other embodiment of the device of the invention. The device 30 comprises a frame which comprises a central area 31, a left lateral area 33 and a right lateral area 32. Each area of the frame has a contact face adapted to face the skin of a subject (directly or through a cloth which is thin enough not to affect a sensor measurement) and an opposed external face. The areas, and especially the contact faces of the areas, have an upper part, a middle part and a lower part. The central area upper part 31*a* is adapted to face the epigastric part of the abdomen of a subject. The central area lower part 31*c* is adapted to face the hypogastrium region of the abdomen of a subject. Then, the central area middle part 31*b* is adapted to face the umbilic region of the abdomen of a subject. Hence, the central area 31 covers the linea alba 36 of the abdomen. Regarding the left lateral and right lateral area, their upper parts 33*a* and 32*a* are adapted to face the respective left or right hypochondrium regions, the middle parts 33*b* and 32*b* are adapted to face the respective left or right flank regions and the lower parts 33*c* and 32*c* are adapted to face the respective left or right iliac region.

The areas 31, 32, 33 of device 30 may alternatively or additionally have their upper parts adapted to be adjusted on the costal margin of the abdomen of a subject, their lower parts adapted to be adjusted to the iliac crests and/or the pubic symphysis and/or the inguinal region of the abdomen of a subject, and their middle part between the lower and the upper parts.

Accordingly the length of the lower parts, the middle parts and the upper parts of each area along the vertical axis of a subject may be equal between each other, i.e. correspond to about third of the length of the abdomen along its vertical axis. Consequently, as the device is positioned on the abdomen and preferably centered on the umbilic region, the central area may be substantially longer than the left lateral or right lateral area due to the shape of an abdomen, as it can be seen on FIG. 7. Hence, the central area 31 may have an upper part 31*a* adapted to be adjusted to the costal margin, i.e. adjoining the xyphoid process for the central area, and a lower part 31*c* adapted to be adjusted to the pubic symphysis The device 30 comprises a network of thirteen main sensors symbolized by thick black segments, some of which are indicated by reference 35 (an arrow for each sensor would render the figure unclear). The main sensors are placed on the belt (on the face of the belt that is meant to face the abdomen). The main sensors are suitable for measuring local deformations and/or local forces on the surface of the abdomen. These sensors are elongated ones, or tongue-shaped, and are preferably present in all of the nine parts of the areas of the frame 30, i.e. in the upper 31*a*, 32*a*, 33*a*, the middle 31*b*, 32*b*, 33*b*, and the lower 31*c*, 32*c*, 33*c* parts of the central, left lateral and right lateral areas. Some sensors may be long enough to cover partially two parts among the nine parts of the device.

The number of main sensors is not limitative and more (or less) main sensors may be included in the network. Accordingly, the network of main sensors may comprise at least 3 main sensors by area or at least 6 main sensors, or at least 9 main sensors. Such numbers of main sensors in the network of main sensors may be applied to any embodiment of the present invention. In particular, at least one main sensor may be located in each area, preferably with at least one main sensor in one of the upper parts, one main sensor in one of the middle parts, and one main sensor in one the lower parts. In a particular embodiment, the main sensors are located only in two parts of each area, e.g. in each of the upper parts and middle parts of each area, or in each of the upper parts and lower parts of each area, or in each of the middle parts and lower parts of each area. In another embodiment, the device comprises at least two sensors in the upper parts of the areas, e.g. one in the left lateral area and one in the right lateral area, at least two main sensors in the middle parts of the areas, e.g. one in the left lateral area and one in the central area, and at least two main sensors in the lower parts of the areas, e.g. one in the central area and one in the right lateral area. Preferably, the device comprises at least one main sensor in each part of each area of the device, i.e. at least 9 main sensors. Also the dimensions of the main sensors may be different. For example, the length of a sensor may be around five centimeters and the width around five millimeters, and the thickness may be about one millimeter or below one millimeter.

In FIG. 7, the main sensors are positioned in the central, left lateral and right lateral areas with one or multiple sensors by area. In the central area, some of the main sensors are substantially parallel to the longitudinal axis (craniocaudal axis) while some are perpendicular to that axis. The sensors in the right lateral and left lateral areas are substantially perpendicular to the longitudinal axis and substantially parallel to the horizontal axis (frontal axis) although some sensors may have been placed substantially parallel to the longitudinal axis.

The device has been evaluated to determine its reliability regarding the evaluation of the internal abdominal pressure and more particularly to the evolution of the internal abdominal pressure variations. The test has been performed on two anesthetized pigs, with an approved method according to animal ethics. Two female feeder pigs of an average weight of 35 kg and aged 3 months minimum were pre-anesthetized. The pigs were placed supine on a veterinary surgical table. The pigs were mechanically ventilated and hemodynamic parameters such as heart rate and $SaO_2$ were continuously monitored. A laparoscopy was performed at the groin level to allow the positioning of a laparoscopic trocar connected to a $CO_2$ laparoscopic insufflator allowing varying the pressure in the abdomen in a controlled way from 0 to 15 mmHg.

An internal pressure sensor was placed inside the peritoneum through this trocar for the reference measurement of the abdominal internal pressure. The internal pressure sensor was connected to a recording unit at a frequency of 20 Hz. The internal pressure sensor was previous calibrated according to the ambient pressure in the operating room. A device comprising a network of 6 tongue-shaped resistive flex sensors (a type of FSR sensor) was placed around the abdomen of the pigs. A first sensor covered the epigastric region along an axis parallel to the anteroposterior axis of the pig, a second sensor covered the hypogastric region along an axis parallel to the anteroposterior axis of the pig, the other four sensors were placed in the plane of the device perpendicularly to the first and second sensors and each of the other four sensors covered one of the regions among the upper left side, the upper right side, the lower left side and the lower right side.

The network of sensors was connected to a recording unit for recording at a frequency of 20 Hz.

The following steps were followed: a stabilization step without insufflation (rest period) of 5 minutes; a step of pressure increase by levels of 6, 12 and 15 mmHg, achieved by insufflation of $CO_2$ into the intraperitoneal cavity with a stabilization step of 2 minutes at each step; a phase of pressure decrease by levels of 12, 6 and 0 mmHg with a stabilization period of 2 minutes at each step; a step of manual pressures applies on the animal's abdomen; a step of mechanical ventilation with an artificial respirator during one minute; a step of pressure increase from 0 to 15 mm Hg without levels followed by a step of pressure decrease from 15 to 0 mmHg, the last step being repeated twice.

The correlation between the abdominal internal pressure measured by the internal pressure sensor and the signal measured by the device main sensors was evaluated using the Pearson linear correlation coefficient (r) for each animal. The Bland-Altman graphical method was used to determine the limits of agreement between the different measurements (±1.96 standard deviations of the differences between measurements).

A correlation study was performed to compare the signals from the main sensors with the internal pressure sensor. The Pearson correlation coefficients are presented in Table 1.2.

TABLE 1.2

| Sensor | Pig 1 | Pig 2 | Mean |
|---|---|---|---|
| Lower right | 0.78 | 0.50 | 0.64 ± 0.20 |
| Upper right | 0.79 | 0.36 | 0.58 ± 0.30 |
| Hypogastric | 0.08 | 0.84 | 0.46 ± 0.54 |
| Epigastric | 0.95 | 0.22 | 0.59 ± 0.52 |
| Lower left | 0.78 | 0.82 | 0.80 ± 0.03 |
| Upper left | 0.37 | 0.85 | 0.61 ± 0.34 |
| Mean | 0.62 ± 0.33 | 0.60 ± 0.28 | |

Figure 8:
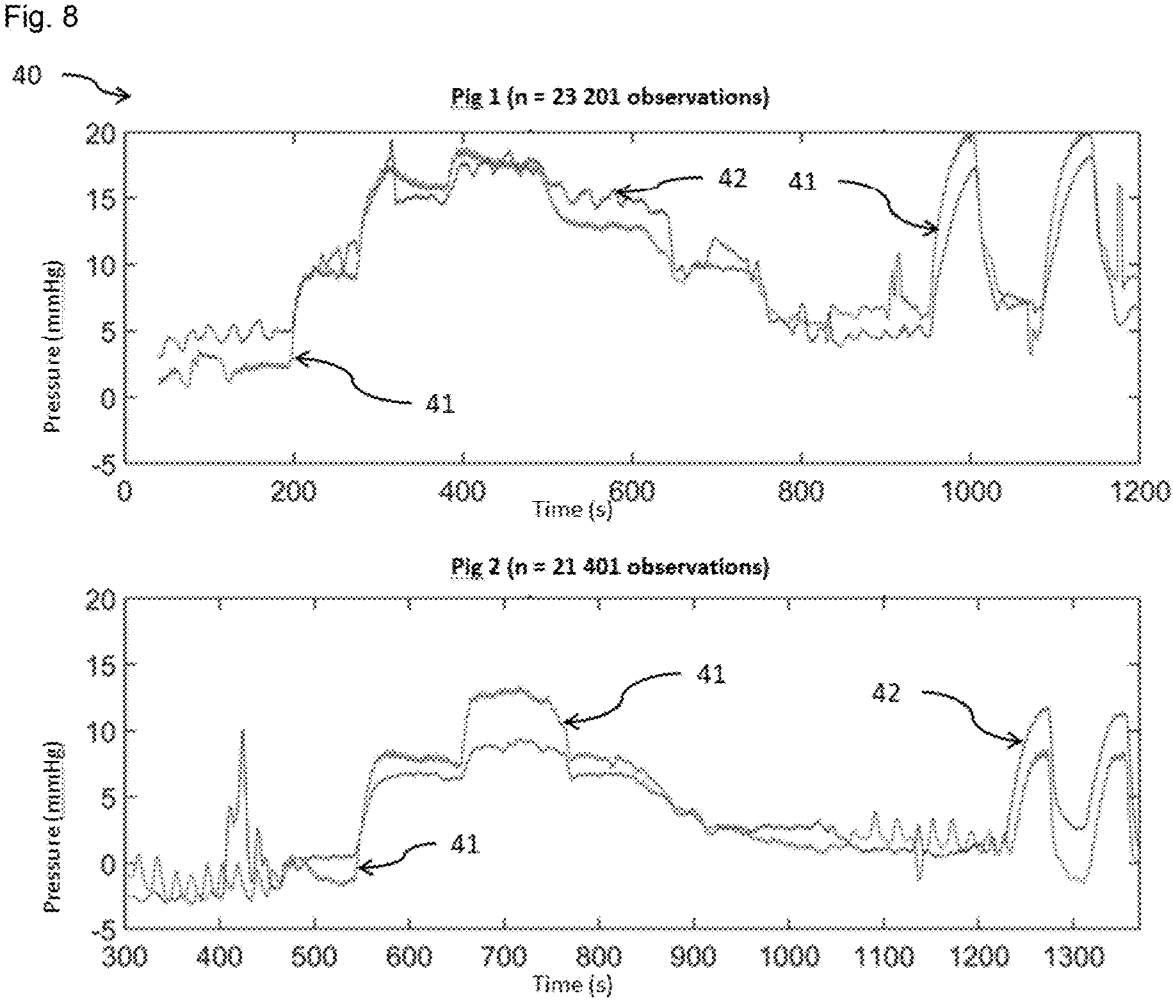
FIG. 8 comprises two graphs representing the internal abdominal pressure as measured by an internal pressure sensor and as measured from the converted signal received by a network of sensors of a device or system according to the invention.

In the graphs 40 in FIG. 8 the internal abdominal pressure is shown as measured by the internal pressure sensor according to curve 42 and as measured from the converted signal received by the network of sensors of the device of the invention according to curve 41. It can be observed from curves 41 and 42 that the measured internal pressure (converted signal or directly measured) is affected during the test duration by the different steps followed (stabilization, pressure increase, insufflation, etc.). A good overall superposition of the signals over the whole test duration, according to the experiments on the two pigs, can be observed. Based on these data, the inventors confirmed that a network of sensors such as tongue-shaped FSR sensors placed to cover an abdomen of a mammal is reliable for assessing an internal abdominal pressure or its evolution in function of time and determining the abdominal wall dynamic biomechanical behavior of a subject.

Figure 9:
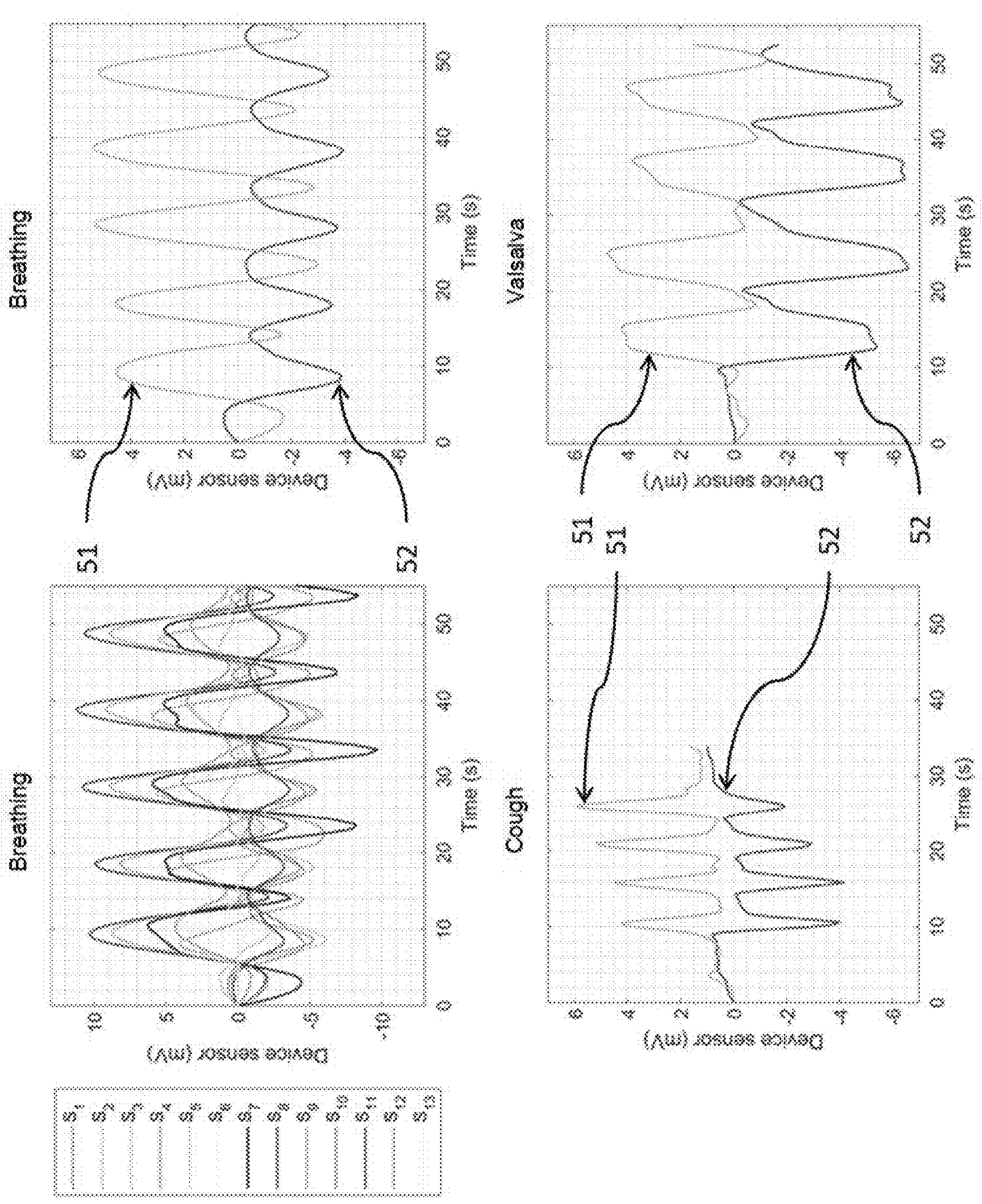
FIG. 9 shows four graphs representing the electric signals or averaged electric signals received by the main sensors of a device of the invention comprising 13 main sensors, during several repetitions of exercises by a subject.

FIG. 9 shows four graphs representing the electric signals or averaged electric signals received by the main sensors of a device of the invention comprising 13 main sensors, during several repetitions of exercises by a subject. The first exercise corresponds to breathing and is represented in the upper left corner and the upper right corner of FIG. 9. The second exercise corresponds to coughing and is represented in the lower left corner of FIG. 9. The third exercise corresponds to the performance of the Valsalva maneuver and is represented in the lower right corner part of FIG. 9. In the upper left corner graph are represented the electric signals received by the 13 main sensors, named from $S_1$ to $S_{13}$, at least one main sensor being located in each area of the frame of the device (i.e. each area comprises at least one main sensor).

In the other graphs (the graphs of the upper right corner, the lower left corner and the lower right corner) are represented the averaged electric signals received by the 13 main sensors, these sensors being regrouped under two groups which are (i) the main sensors located in the left or right lateral areas of the frame, and (ii) the main sensors located in the central area of the frame. Curve 51 corresponds to the evolution over time of the averaged electric signals received by the main sensors which are located in the central area of the frame, while curve 52 corresponds to the evolution over time of the averaged electric signals received by the main sensors which are located in the left lateral or right lateral area.

Figure 10:
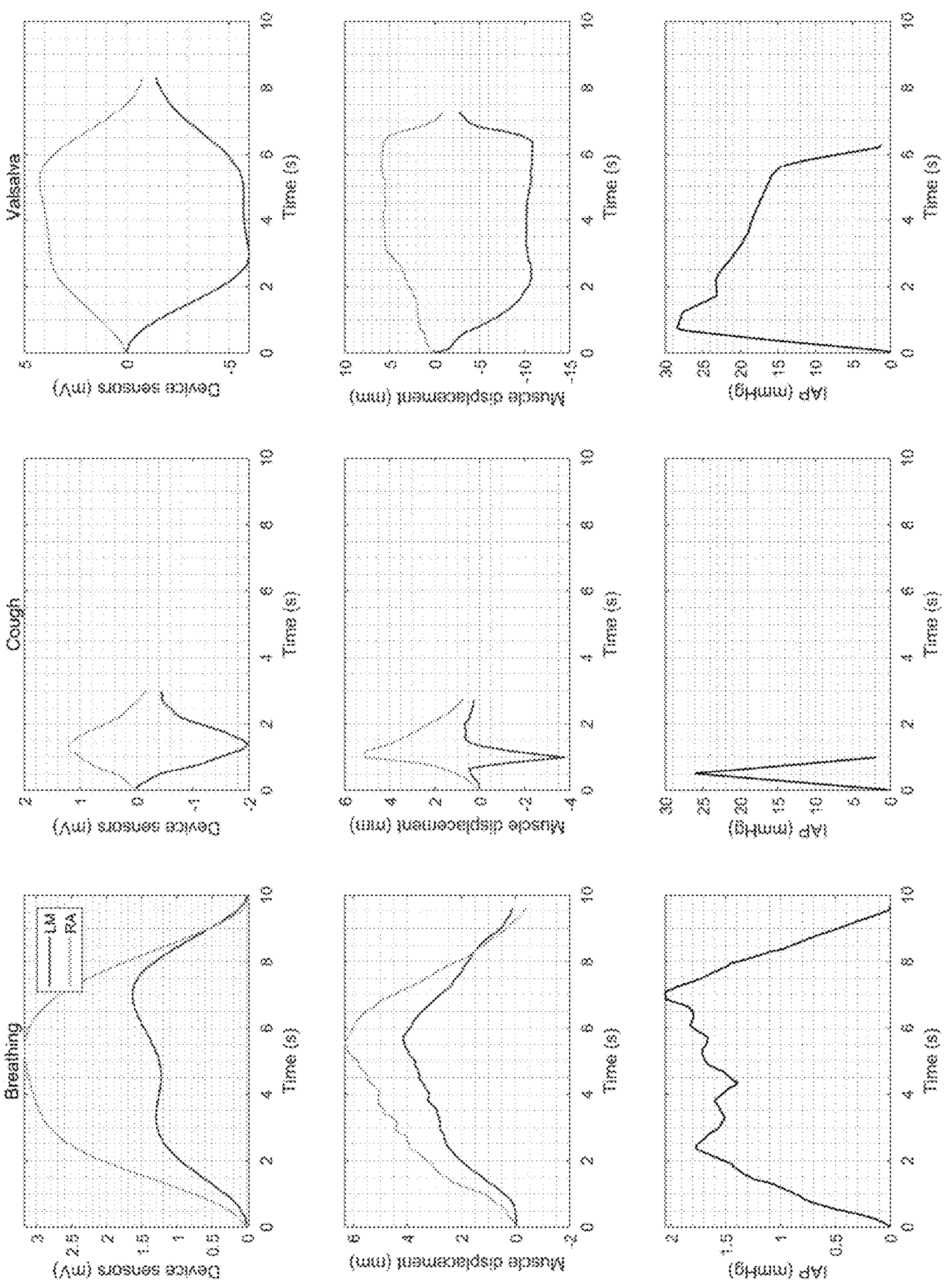
FIG. 10 shows a comparison between three graphs representing the averaged electric signals received by the main sensors of a device of the invention, three graphs representing muscle displacements measurements obtained from MRI methods and three graphs representing intra-abdominal pressure measurements obtained from connected pressure sensors (motility capsules collecting data from the gastro-intestinal tract).

FIG. 10 shows a comparison between three graphs representing the averaged electric signals received by the main sensors of a device of the invention, three graphs representing muscle displacements measurements obtained from MRI methods and three graphs representing intra-abdominal pressure measurements obtained from connected pressure sensors (motility capsules collecting data from the gastrointestinal tract). These graphs demonstrate similar evolutions of the parameters measured and demonstrate that the device of the invention allows evaluating and/or monitoring an intra-abdominal pressure and/or abdominal wall deformations and/or a risk of incisional hernia of a subject without the need for heavy means or uncomfortable means.

The present invention is not limited to the embodiments described above but extends to any embodiment falling within the scope of the claims.

The invention claimed is:

1. A system for non-invasively evaluating or monitoring an intra-abdominal pressure and/or a risk of incisional hernia of a subject at a preventive stage and/or a pre-operative stage and/or a post-operative stage, the system comprising a device and a treatment unit connected to the device, said device comprising:

an adjustable and flexible frame, the frame comprising a central area, a left lateral area and a right lateral area, each area having a contact face adapted to face the skin of a subject and an opposed external face;

a network of main sensors suitable for measuring local deformations and/or local forces on the surface of the abdomen of the subject, said network of main sensors being assembled to the frame, wherein at least one main sensor is located in each area of the frame;

connecting means adapted for connecting said network of main sensors to a treatment unit;

wherein the treatment unit comprises means for recording and analyzing all or part of the measured local deformations and/or local forces on the surface of the subject and correlating the measured local deformations and/or local forces on the surface of the abdomen of the subject with deep muscular wall behaviors, the treatment unit further comprising means of determination of a level of risk of rupture in an abdominal wall.

2. The system as claimed in claim 1, wherein the contact face of each area has an upper part adapted to face an hypochondrium or an epigastric part of the abdomen of a subject, a lower part adapted to face the hypogastrium region or an iliac part of the abdomen of a subject, and a middle part adapted to face the umbilic region or a flank part of the abdomen of a subject; and wherein the upper parts are adapted to be adjusted on the costal margin of the abdomen of a subject, the lower parts are adapted to be adjusted to the iliac crests and/or the pubic symphysis and/or the inguinal region of the abdomen of a subject, and the middle parts between the lower and the upper parts.

3. The system as claimed in claim 2, wherein at least one main sensor is located in each part of each area of the frame.

4. The system as claimed in claim 1, further comprising at least an adjustment sensor suitable for measuring an adjustment parameter of the device on the abdominal wall, and means for connecting said at least one adjustment sensor to the treatment unit.

5. The system as claimed in claim 4, wherein the adjustable and flexible frame is a belt, wherein the adjustment parameter of the device corresponds to the belt tightening tension, and adjustment means may be hook and loop material tapes on the belt, push-buttons, or straps.

6. The system as claimed in claim 1, wherein the main sensors and/or the at least one adjustment sensor is a resistive sensor, for instance a force sensing resistor (FSR) sensor or another piezoresistive sensor, a piezoelectric sensor, a pneumatic sensor, an electromyography (EMG) sensor, a capacitive sensor or a combination of several of said sensors, preferably a force sensing resistor (FSR) sensor.

7. The system as claimed in claim 1, the device being a connected-device and comprising a wired and/or wireless network communication interface.

8. The system as claimed in claim 1, wherein the adjustable and flexible frame is a belt, preferably an elastic belt.

9. The system as defined in claim 1, wherein the treatment unit is able to:

display all or part of the measured local deformations and/or local forces, and/or select some of the main sensors, and/or control and/or adjust the adjustment parameter of the device on the abdominal wall.

10. The system as claimed in claim 1, the device further comprising on-board electronics connected with a wired connection to the main sensors and/or the at least one adjustment sensor, said on-board electronics being wireless connected to the treatment unit.

11. A method for non-invasively evaluating or monitoring an intra-abdominal pressure and/or a risk of incisional hernia of a subject at a preventive stage and/or a pre-operative stage and/or a post-operative stage, said method using a system as defined in claim 1, and comprising:

a positioning step adapted to position the device on the abdomen of a subject in such a way that the main sensors face the abdominal wall, said main sensors being placed on the abdominal wall;

a measuring step adapted to measure local deformations and/or local forces on the surface of the abdomen at different times, for at least a given period of time, in order to obtain a temporal evolution of the local deformations and/or local forces;

a correlation step adapted to correlate the measured local deformations and/or local forces with the mechanical behavior of the deep muscular wall, and further comprising a step of determining a level of risk of rupture in the abdominal wall.

12. The method as claimed in claim 11, wherein the device comprises a network of main sensors being different types of main sensors and wherein the measuring step comprises measuring local deformations and local forces at different areas (A1, A2, A3) of the abdominal wall.

13. The method as claimed in claim 11, comprising a step of performing exercises in which the subject performs different predefined exercises during all or part of the measuring step.

14. The method as claimed in claim 11, comprising a comparing step, adapted to compare all of part of the measured local deformations and/or local forces to reference values, said reference values being based on values of local deformations and/or local forces available for at least another subject or a panel of subjects.

* * * * *